United States Patent
Xu

(10) Patent No.: US 11,389,475 B2
(45) Date of Patent: Jul. 19, 2022

(54) METHOD FOR INDUCING AN M1 DOMINATED IMMUNE RESPONSE AND PHARMACEUTICAL COMPOSITIONS

(71) Applicant: Minzhen Xu, Weehawken, NJ (US)

(72) Inventor: Minzhen Xu, Weehawken, NJ (US)

( * ) Notice: Subject to any disclaimer, the term of this patent is extended or adjusted under 35 U.S.C. 154(b) by 154 days.

(21) Appl. No.: 16/629,642

(22) PCT Filed: Jul. 13, 2018

(86) PCT No.: PCT/US2018/041922
§ 371 (c)(1),
(2) Date: Jan. 9, 2020

(87) PCT Pub. No.: WO2019/014511
PCT Pub. Date: Jan. 17, 2019

(65) Prior Publication Data
US 2021/0137976 A1    May 13, 2021

Related U.S. Application Data

(60) Provisional application No. 62/532,465, filed on Jul. 14, 2017.

(51) Int. Cl.
*A61K 39/00* (2006.01)
*A61K 35/16* (2015.01)
*A61P 37/02* (2006.01)

(52) U.S. Cl.
CPC ............. *A61K 35/16* (2013.01); *A61K 39/00* (2013.01); *A61P 37/02* (2018.01); *A61K 2039/57* (2013.01)

(58) Field of Classification Search
CPC .................................................... A61K 35/16
See application file for complete search history.

(56) References Cited

U.S. PATENT DOCUMENTS

| | | | |
|---|---|---|---|
| 9,139,652 B2 | 9/2015 | Haegel et al. | |
| 2010/0135975 A1* | 6/2010 | Yu ........................... | A61P 37/04 424/93.71 |
| 2017/0056430 A1 | 3/2017 | Andrews et al. | |

FOREIGN PATENT DOCUMENTS

| KR | 10-2016-0010450 A | 1/2016 |
|---|---|---|
| WO | 2015-081253 A1 | 6/2015 |

OTHER PUBLICATIONS

Chen et al. (Oncology Reports vol. 20, pp. 979-985) (Year: 2008).*
Genin, M. et al. "M1 and M2 macrophages derived from THP-1 cells differentially modulate the response of cancer cells to etoposide", 2015, BMC Cancer, 15, article 577, pp. 1-14.
Hedbrandt, A. et al. "Macrophages of M1 phenotype have properties that influence lung cancer cell progression", 2015, Tumor Biol., 36, pp. 8715-8725.
Rhee, Inmoo, "Diverse macrophages polarization in tumor microenvironment", 2016, Arch. Pharm. Res., 39, pp. 1588-1596.
Brown et al., The promise of targeting macrophages in cancer therapy, 2017, Clinical Cancer Research, 23(13), pp. 3241-3250.
Epelman S. et al., Origin and functions of tissue macrophages, 2014, Immunity, 41(1) pp. 21-35.
Hanahan, D. et al., Hallmarks of cancer: the next generation, 2011, Cell, 144(5), pp. 646-674.
Heusinkveld, M. et al., M2 macrophages induced by prostaglandin E2 and IL-6 from cervical carcinoma are switched to activated M1 macrophages by CD4+ Th1 cells, 2011, The Journal of Immunology, 187, pp. 1157-1165.
Marelli G. et al., Inflammation as target in cancer therapy, 2017, Current Opinion in Parmacology 35, pp. 57-65.
Mills C.D. et al., A breakthrough: macrophage-directed cancer immunotherapy, 2016, Cancer Research, 76(3), pp. 513-516.
Mills, C.D. et al., M-1/M-2 macrophages and the Th1/Th2 paradigm, 2000, The Journal of Immunology, 164, pp. 6166-6173.
Tariq M. et al., Macrophage polarization: anti-cancer sliategies to target tumor-associated macrophage in breast cancer, 2017, Journal of Cell Biochemistry, 118, pp. 2484-2501.
Watanabe, H. et al., Innate immune response in Th1- and Th2-dominant mouse strains, 2004, Shock, 22(5), pp. 460-466.
International Search Report, PCT/US2018/041922, dated Feb. 28, 2019.
Loppnow, H. et al. "Cytokine induction by lipopolysaccharide (LPS) corresponds to lethal toxicity and is inhibited by nontoxic Rhodobacter capsulatus LPS", 1990, Infect Immun., 58(11), pp. 3743-3750.
Amiot, F. et al. "Lipopolysaccharide-induced cytokine cascade and lethality in LT alpha/TNF alpha-deficient mice", 1997, Mol. Me. 3(12), pp. 864-875.
Lim, K-H. et al. "Toll-Like Receptor Signaling", 2013, Cold Spring Harbor Perspective in Biology, 5(1):a011247.
Ozato, K. et al. "Toll-like receptor signaling and regulation of cytokine gene expression in the immune system", 2002, Biotechniques, 33, pp. s66-s75.
Chattopadhyay, S. et al., "Tyrosine Phosphorylation in Toll-Like Receptor Signaling", 2014, Cytokine Growth Factor Rev., 25(5), pp. 533-541.
Ross, S.H. et al. "Signaling and Function of Interleukin-2 in T Lymphocytes", 2018, Annu. Rev. Immunol., 36, pp. 411-433.
Tonkonogy, L. et al. "Stimulation of gut-associated lymphoid cells by IL-4 and B-cell growth factor II S", 1988, Immunology, 54, pp. 155-161.

* cited by examiner

*Primary Examiner* — Albert M Navarro
(74) *Attorney, Agent, or Firm* — Wiggin and Dana LLP; Anthony Sabatelli

(57) ABSTRACT

The present invention relates to the field of immunology and to methods for inducing an M1/Th1 dominated immune response in an M2 macrophage dominated and/or Th2/Treg dominated human patient or animal. These methods are useful for developing therapies for treating or preventing M2 macrophage mediated and/or Th2/Treg mediated disease states.

4 Claims, No Drawings

METHOD FOR INDUCING AN M1 DOMINATED IMMUNE RESPONSE AND PHARMACEUTICAL COMPOSITIONS

FIELD OF THE INVENTION

The present invention relates to the field of immunology and to methods for inducing an M1 dominated immune response in an M2 dominated human patient or animal. These methods are useful for developing therapies for treating or preventing M2 macrophage mediated disease states. The methods are useful for developing therapies for treating various forms of cancer and other immune-related diseases. The present invention also relates to an immune activated allogenic or xenogenic sera for treating cancers and other diseases, and to methods for treating cancers or other diseases by administering to a human or animal in need thereof such immune activated allogenic or xenogenic sera, with or without an immunogen, for the induction of an M1-dominated immune response in the M2 dominated human or animal.

BACKGROUND OF THE INVENTION

Macrophages are multifunctional cells found throughout the body in different tissues where they contribute to tissue development, remodeling and homeostasis [1, Epelman et al., 2, Brown et al.]. These cells survey the local environment, secrete trophic factors, phagocytose cells and debris, and carry out repairs to maintain homeostasis. Macrophages undergo a remarkable degree of transcriptional reprogramming in response to local cues to adapt their phenotype and function. The high degree of plasticity of macrophages renders them easily transformable into different phenotypes and functions for maintaining homeostasis. However, this high degree of plasticity can be problematic when normal regulatory mechanisms fail in different disease states, and in some cases rending macrophages to lose their normal function of maintaining homeostasis and turning them into disease promoting agents in conditions such as cancer.

Macrophages are important compounds in innate immune responses [4, Tariq et al., 5, Mills et al.]. Despite a broad spectrum of ways to activate macrophages, there are two main groups designated M1 (classically activated) macrophages and M2 (alternatively activated) macrophages. Macrophages are activated into M1 macrophages in normal immune background individuals upon the phagocytosis, i.e. the ingestion, of microorganisms. Under these conditions, macrophages are stimulated through the toll-like receptor (TLR) ligands, such as pathogen-associated molecular patterns (PAMPs) including lipopolysaccharides (LPS) from the phagocytosed microorganisms. The M1 macrophages are characterized by the secretion of pro-inflammatory cytokines and reactive nitrogen and oxygen species. M1 macrophages possess bactericidal and anti-tumor activity and thus they are one of the main forces in innate immune responses to fight against invading microorganisms and other cellular abnormalities such as cancers. M1 macrophages secrete high levels of interleukin (IL)-12 and low levels of IL-10. In contrast, the Th2 cytokines IL-4 and IL-13 polarize macrophages toward an anti-inflammatory M2 phenotype. M2 macrophages turn off damaging immune responses by producing anti-inflammatory cytokines like IL-10 and, meanwhile, execute the functions involved in constructive processes like tissue repair and healing of wounds. M2 macrophages produce high levels of IL-10, TGF-beta and low levels of IL-12. M1 and M2 macrophages are orchestrated in a normal immune background individual to fight invaders (e.g. microorganisms and virus infected cells) and clean abnormal substances (e.g. tumor cells and oxidized LDL) and reconstruct local tissues. The activation of M1 and M2 macrophages must be balanced—like the yin-yang—in the homeostasis of tissues.

Macrophages play an important role in activating and balancing adaptive immune responses [4, Tariq et al., 5, Mills et al.]. Upon activation, M1 macrophages express high level MHC class II molecules. M1 macrophages process phagocytosed microorganisms and then present the antigens from these processed microorganisms or tumor cells, in the context with MHC class II molecules, to activate type 1 T-helper cells (Th1). M1 macrophages activate the Th1 responses that can further conversely amplify M1 macrophage activity through the production of IFN-γ by Th1 cells (a feedback loop). If specific antigens, such as tumor antigens, are present, M1 macrophage-directed adaptive immunity can result in the stimulation of tumor-specific cytotoxic T cells (Tcytotoxic). The antigen non-specific M1-dominant macrophages and antigen-specific Th1/Tcytotoxic cells form a strong network to fight invading microorganisms and abnormalities occurring inside the body. In contrast, M2 macrophages, through innate signals such as TGF-β and IL-10, induce T cells to transform into type 2 T-helper cells (Th2) and T regulatory cells (Treg). The Th1/Tcytotoxic and Th2/Treg arms of adaptive immune systems are two main compounds of the antigen-specific immune response. These two arms are orchestrated harmoniously in those individuals with normal immune backgrounds, exhibiting a balanced immune response.

Macrophage activity is important in disease states. Affected by local disease states such as cancer, the recruited macrophages are abundantly transformed into M2 macrophages [4, Tariq et al. 5, Mills et al.]. M2 macrophage dominated innate immune responses lead to an unbalanced adaptive immune response, e.g. prevailed Th2 and Treg. The M2 macrophages, Th2, and Treg form a suppressed immune response network that strongly suppress the M1, Th1, and Tcytotoxic immune response in patients with cancer. Strategies targeting macrophages can be a way to breakdown the M2 dominated immune background in patients with cancer, because it could cut off the origin of the suppressed immune response. Tumor-associated macrophages (TAMs) are the most abundant M2 macrophages in the tumor microenvironment. TAMs contribute to tumor progression at almost all different levels: 1) promoting genetic instability; 2) nurturing cancer stem cells; 3) enhancing angiogenesis; 4) exerting immunosuppression and taming protective adaptive immunity, and 5) supporting tumor invasion and metastasis. Clinical studies have documented the association between the high influx of TAMs in tumors with poor prognosis in hepatocellular, ovarian, cervical, and breast cancer. Studies have also shown that TAMs produce a high level of anti-inflammatory factors which are directly responsible for the development of tumors.

Due to their high degree of plasticity, macrophages easily accept the "education" from tumor cells and the tumor microenvironment to become the assistants or accomplices of the tumor cells. Macrophages help the tumor cells to complete the above functions that the tumor cells need to complete for their survival and expansion, but are unable to complete. Thus, TAMs play pivotal roles in directing cancer outcomes. Targeting TAMs can provide new approaches for cancer immunotherapy.

Macrophage targeted approaches to anticancer therapy are under investigation, and include inhibition of macrophage recruitment to, and/or survival in, tumor microenvironments; reprogramming of TAMs to become an anti-tumor, M1 like microphage; and tumor-targeting monoclonal antibodies that elicit macrophage-mediated extracellular killing, or phagocytosis and intracellular destruction of cancer cells. [3, Marelli et al., 4, Tariq et al., 5, Mills et al.]: TAM-focused therapeutic strategies have the potential to complement and synergize with both chemotherapy and immunotherapy.

Although evidence indicates that targeting macrophage responses is a breakthrough that will facilitate successful immunotherapy, there are still many hurdles to overcome to develop safe and effective therapies. 1) Efficacy or effectiveness is the first goal that needs to be achieved. Many macrophages targeting approaches do not have apparent affectivity. This lack of efficacy could be due to heterogenicity of the macrophages in vivo. A single method is not sufficient to transform all M2 macrophages into M1 like macrophages to overcome the established M2 dominated background. 2) Simplicity is another goal that needs to be achieved before the therapies can be clinically used. Many studies have attempted to isolate M2 macrophages and then retransforming them in vitro into M1-like macrophages and then transfuse them back into the patients. However, these are very complex procedures, and they are not practical for routine clinical use. 3) The in vivo induction of an M1 dominated immune response in M2 dominated patients can avoid many unnecessary procedures. For example, attempts at stimulating a macrophage/innate immunity with the injection of inactivated microorganisms (Coley's Toxin) has been performed. However, this strategy was accompanied by dangerous side-effects that have also been observed in more recent attempts at immunotherapy. 4) Existing strategies for targeting macrophages tend to be focused solely on a patient's own immune response, and can greatly hampered the induction of an M1 dominated immune response in an M2 dominant individual.

Previous studies have not been effective because of the heterogeneity of TAMs. Many studies have used in vitro approaches which are not practical for clinical use, and thus in vivo approaches are superior. Most studies have focused on the use of a patient's own immune system, which is already hampered by their M2 dominant immune response.

It is seen from the foregoing that there are many disadvantages to current therapies and much work that needs to be done to develop effective therapies. The present invention proposes a different solution which seeks to overcome previous deficiencies. The present invention utilizes an in vivo approach using immune activated sera from a healthy individual with a M1 dominant immune background to induce and M1 dominated immune response in an M2 dominated patient. The details will be described below.

SUMMARY OF THE INVENTION

The present invention relates to the field of immunology and to methods for inducing an M1 dominated immune response in an M2 dominated human patient or animal. These methods are useful for developing therapies for treating or preventing M2 macrophage mediated disease states.

We surprisingly found in the present invention that it is possible to induce an M1 dominated immune response in an M2 dominated human or animal. This induction has practical applicability for treating or preventing a wide range of M2 macrophage mediated disease states or conditions.

DETAILED DESCRIPTION OF THE INVENTION

The present invention relates to a method for inducing an M1 dominated immune response in an M2 dominated patient comprising the steps of:
(a) obtaining an immune active allogenic or xenogenic serum sample from a healthy donor subject; and
(b) transfusing the serum sample into the M2 dominated patient, wherein the time schedule (regimen) for obtaining the serum sample and the time schedule (regimen) for transfusing the serum sample model the natural time course of the immune response induction against an acute infection caused by a virus or bacteria.

In another aspect the present invention relates to a method wherein the M2 dominated patient has been immunized with an immunogen prior to transfusing the serum sample.

In another aspect the present invention relates to a method wherein the M2 dominated patient has not been immunized with an immunogen prior to transfusing the serum sample.

In another aspect the present invention relates to a method wherein the healthy donor subject has a normal immune response background.

In another aspect the present invention relates to a method wherein the healthy donor subject is inoculated with an immunogen or immunogens or infected with (viable) microorganisms prior to obtaining the serum sample of step (a).

In another aspect the present invention relates to a method wherein the time schedule for obtaining the serum sample of step (a) and the time schedule for transfusing the serum sample of step (b) are each individually selected from about 8 hours to about 14 days after inoculation of the donor subject.

In another aspect the present invention relates to a method wherein the time schedules are each individually selected from about 8 hours, 24 hours, 48 hours, 96 hours, 168 hours, and 192 hours.

In another aspect the present invention relates to a method for treating an M2 macrophage mediated disease state in a patient in need thereof comprising the steps of:
(a) obtaining an immune active serum sample from a healthy donor subject (other than the patient); and
(b) transfusing the serum sample into the patient, wherein the time schedule (regimen) for obtaining the serum sample and the time schedule (regimen) for transfusing the serum sample model the natural time course of the immune response induction against an acute infection caused by a virus or bacteria.

In another aspect the present invention relates to a method wherein said disease state is selected from cancer, chronic viral infections, allergies, and asthma.

In another aspect the present invention relates to a method wherein the disease state is cancer.

In another aspect the present invention relates to a method further comprising treating the patient with an existing (conventional) cancer therapy.

In another aspect the present invention relates to a method wherein the existing cancer therapy is selected from chemotherapy, radiation therapy, immunotherapy, and combinations thereof.

In another aspect the present invention relates to a method wherein the M2 dominated patient and the healthy donor are both mammals.

In another aspect the present invention relates to a method wherein the M2 dominated patient and the healthy donor are both humans.

In another aspect the present invention relates to a method wherein the M2 dominated patient is a human.

In another aspect the present invention relates to a therapeutic serum for inducing an M1 dominated immune response in an M2 dominated patient comprising a serum sample obtained from a healthy donor wherein the donor has been inoculated with an immunogen.

In another aspect the present invention relates to a pharmaceutical composition comprising a therapeutic serum according to the present invention.

In another aspect the present invention relates to a pharmaceutical composition further comprising active factors that are essential for the induction of M1 dominated immune response in vivo.

In another aspect the present invention relates to a pharmaceutical composition wherein said active factors are selected from cytokines, chemokines, growth factors, macrophage activating factors, enzymes, and combinations thereof.

In another aspect the present invention relates to a method wherein the sera are allogenic sera.

In another aspect the present invention relates to a method wherein the sera are xenogenic sera.

In another aspect the present invention relates to a therapeutic serum that is an allogenic serum.

In another aspect the present invention relates to a therapeutic serum that is a xenogenic serum.

In another aspect the present invention relates to a pharmaceutical composition wherein the serum is an allogenic serum.

In another aspect the present invention relates to a pharmaceutical composition wherein the serum is xenogenic serum.

In another aspect the present invention relates to the use of a therapeutic serum for the manufacture of a medicament for inducing an M1 dominated immune response in an M2 dominated patient comprising a serum sample obtained from a healthy donor wherein the donor has been inoculated with an immunogen.

In another aspect the present invention relates to a method for inducing a TH1 and Tcytotoxic immune response in an M2/Th2 dominated patient comprising the steps of:
(a) obtaining an immune active allogenic or xenogenic serum sample from a healthy donor subject; and
(b) transfusing the serum sample into the M2/Th2 dominated patient,
wherein the time schedule (regimen) for obtaining the serum sample and the time schedule (regimen) for transfusing the serum sample model the natural time course of the immune response induction against an acute infection caused by a virus or bacteria.

In another aspect the present invention relates to a method for treating an M2 macrophage or Th2 mediated disease state in a patient in need thereof comprising the steps of:
(a) obtaining an immune active serum sample from a healthy donor subject (other than the patient); and
(b) transfusing the serum sample into the patient,
wherein the time schedule (regimen) for obtaining the serum sample and the time schedule (regimen) for transfusing the serum sample model the natural time course of the immune response induction against an acute infection caused by a virus or bacteria.

In another aspect the present invention relates to a therapeutic serum for inducing a Th1 and Tcyctotoxic immune response in an M2/Th2 dominated patient comprising a serum sample obtained from a healthy donor wherein the donor has been inoculated with an immunogen.

In another aspect the present invention relates to the use of a therapeutic serum for the manufacture of a medicament for inducing a Th1 and Tcytotoxic immune response in an M2/Th2 dominated patient comprising a serum sample obtained from a healthy donor wherein the donor has been inoculated with an immunogen.

In another aspect the present invention relates to a method for manufacturing a medicament for inducing an M1 dominated immune response in an M2 dominated patient comprising the steps of:
(a) obtaining an immune active allogenic or xenogenic serum sample which is obtained from a healthy donor subject; and
(b) formulating said serum sample as an active ingredient in an effective amount to form a therapeutic serum preparation for use in transfusing into the M2 dominated patient to induce the M1 dominated immune response,
wherein the time schedule (regimen) for obtaining the serum sample and the time schedule (regimen) for transfusing the serum sample model the natural time course of the immune response induction against an acute infection caused by a virus or bacteria.

In another aspect the present invention relates to a method wherein the M2 dominated patient has been immunized with an immunogen prior to transfusing the serum sample.

In another aspect the present invention relates to a method wherein the M2 dominated patient has not been immunized with an immunogen prior to transfusing the serum sample.

In another aspect the present invention relates to a method wherein the healthy donor subject has a normal immune response background.

In another aspect the present invention relates to a method wherein the healthy donor subject is inoculated with an immunogen or immunogens or infected with (viable) microorganisms prior to obtaining the serum sample therefrom.

In another aspect the present invention relates to a method wherein the time schedule for obtaining the serum sample from the donor subject and the time schedule for transfusing the therapeutic serum preparation are each individually selected from about 8 hours to about 14 days after inoculation of the donor subject.

In another aspect the present invention relates to a method wherein the time schedules are each individually selected from about 8 hours, 24 hours, 48 hours, 96 hours, 168 hours, and 192 hours.

In another aspect the present invention relates to a method for manufacturing a medicament for treating an M2 macrophage mediated disease state in a patient in need thereof comprising the steps of:
(a) providing an immune active serum sample which is obtained from a healthy donor subject (other than the patient); and
(b) formulating said serum sample as an active ingredient in an effective amount to form a therapeutic serum preparation for use in transfusing into the patient to treat the M2 macrophage mediated disease state,
wherein the time schedule (regimen) for obtaining the serum sample and the time schedule (regimen) for transfusing the serum sample model the natural time course of the immune response induction against an acute infection caused by a virus or bacteria.

In another aspect the present invention relates to a method wherein said disease state is selected from the group consisting of cancer, chronic viral infections, allergies, and asthma.

In another aspect the present invention relates to a disease state is cancer.

In another aspect the present invention relates to a method wherein the medicament is administered to the patient in combination with an existing (conventional) cancer therapy.

In another aspect the present invention relates to a method wherein the existing cancer therapy is selected from the group consisting of chemotherapy, radiation therapy, immunotherapy, and any combinations thereof.

In another aspect the present invention relates to a method wherein the M2 dominated patient and the healthy donor are both mammals.

In another aspect the present invention relates to a method wherein the M2 dominated patient and the healthy donor are both humans.

In another aspect the present invention relates to a method wherein the M2 dominated patient is a human.

In another aspect the present invention relates to a therapeutic serum preparation for inducing an M1 dominated immune response in an M2 dominated patient comprising an effective amount of a serum sample as an active ingredient which is obtained from a healthy donor wherein the donor has been inoculated with an immunogen.

In another aspect the present invention relates to a pharmaceutical composition comprising a therapeutic serum preparation according to the present invention.

In another aspect the present invention relates to a pharmaceutical composition further comprising active factors that are essential for the induction of M1 dominated immune response in vivo.

In another aspect the present invention relates to a pharmaceutical composition wherein said active factors are selected from the group consisting of cytokines, chemokines, growth factors, macrophage activating factors, enzymes, and any combinations thereof.

In another aspect the present invention relates to a method according to the present invention wherein the sera are allogenic sera.

In another aspect the present invention relates to a method according to the present invention wherein the sera are xenogenic sera.

In another aspect the present invention relates to a therapeutic serum preparation that is an allogenic serum.

In another aspect the present invention relates to a therapeutic serum preparation that is a xenogenic serum.

In another aspect the present invention relates to a pharmaceutical composition wherein the serum is an allogenic serum.

In another aspect the present invention relates to a pharmaceutical composition wherein the serum is a xenogenic serum.

In another aspect the present invention relates to a the use of a therapeutic serum preparation for the manufacture of a medicament for inducing an M1 dominated immune response in an M2 dominated patient, said therapeutic serum preparation comprising a serum sample which is obtained from a healthy donor wherein the donor has been inoculated with an immunogen.

In another aspect the present invention relates to a method for manufacturing a medicament for inducing a TH1 and cytotoxic immune response in an M2/Th2 dominated patient comprising the steps of:
(a) providing an immune active allogenic or xenogenic serum sample which is obtained from a healthy donor subject; and
(b) formulating said serum sample as an active ingredient in an effective amount to form a composition for use in transfusing the serum sample into the M2/Th2 dominated patient to induce the TH1 and cytotoxic immune response, wherein the time schedule (regimen) for obtaining the serum sample and the time schedule (regimen) for transfusing the serum sample model the natural time course of the immune response induction against an acute infection caused by a virus or bacteria.

In another aspect the present invention relates to a method for manufacturing a medicament for treating an M2 macrophage or Th2 mediated disease state in a patient in need thereof comprising the steps of:
(a) providing an immune active serum sample which is obtained from a healthy donor subject (other than the patient); and
(b) formulating said serum sample as an active ingredient in an effective amount to form a composition for use in transfusing the serum sample into the patient to treat the M2 macrophage or Th2 mediated disease state, wherein the time schedule (regimen) for obtaining the serum sample and the time schedule (regimen) for transfusing the serum sample model the natural time course of the immune response induction against an acute infection caused by a virus or bacteria.

In another aspect the present invention relates to a therapeutic serum preparation for inducing a Th1 and cytotoxic immune response in an M2/Th2 dominated patient comprising an effective amount of a serum sample which is obtained from a healthy donor wherein the donor has been inoculated with an immunogen.

In another aspect the present invention relates to the use of a therapeutic serum preparation for the manufacture of a medicament for inducing a Th1 and cytotoxic immune response in an M2/Th2 dominated patient, said therapeutic serum preparation comprising a serum sample which is obtained from a healthy donor wherein the donor has been inoculated with an immunogen.

Definitions

As used herein, the following terms have the indicated meanings unless expressly stated to the contrary.

The term "allogenic", as used herein, means that the serum or sample is taken from a healthy donor or subject and transferred into another patient recipient or subject in same species. In contrast, the term "xenogenic", as used herein, means that the serum or sample is taken from a subject and transferred to a different subject from different species.

The terms "treat," "treating" or "treatment," as used herein, include alleviating, abating or ameliorating the disease state or condition, or preventing or reducing the risk of contracting the disease state or condition or exhibiting the symptoms of the disease state or condition, ameliorating or preventing the underlying causes of the symptoms, inhibiting the disease state or condition, arresting the development of the disease state or condition, relieving the disease state or condition, causing regression of the disease state or condition, or stopping the symptoms of the disease state or condition, either prophylactically and/or therapeutically.

The term "M1 dominated immune response" as used herein, is one in which M1 macrophages play a key role. As a result, Th1 and Tcytotoxic cells play a key role in same induced immune response. Such treatment can be carried out by administering to a subject in need thereof an effective amount of an active ingredient or a preparation or composition comprising such active ingredient (e.g. a serum sample or a preparation/composition comprising the same, as described herein) to induce a desired effect in the subject (e.g. inducing an M1 dominated immune response, treating a M2 macrophage mediated disease state, and/or inducing a TH1 and cytotoxic immune response, in a subject in need thereof, e.g. an M2 dominated patient, particularly an M2/Th2 dominated patient).

The term "M2 dominated patient" as used herein, is a subject or patient with a disease state or condition in which M2 macrophages play a key role. As a result, Th2 and Treg play a key role in same induced immune response. Examples of these disease states or conditions are cancer, chronic virus infection, and allergy and asthma.

The term "immunogen" as used herein, is an inactivated or recombinant microorganism (bacteria or virus) or their subunit (CpG or LPS). The term "immunogen" as used herein, is a compound of pathogen-associated molecular patterns (PAMPs) other than CpG and LPS.

The term "healthy donor subject" as used herein, is a donor subject who has a normal immune response background.

The terms "patient" and "subject", although primarily intended to include humans, can also include other mammals and also non-mammalian animals such as avian animals. Furthermore, regarding the term "xenogenic" as described above, the transfer of serum or a sample can be between two different species.

M1 and M2 Macrophages and the Immune System

Macrophages and Inflammation. Macrophages have dual roles during inflammation and repair as 1) the primary phagocytes for the removal of invading microorganisms and the debris of apoptotic cells and 2) the agents which perform tissue repair. [1, Epelman et al., 2, Brown et al.] Both these functions of the macrophage are performed by M1 and M2 like macrophages. Circulating monocytes are transformed into M1 macrophages by first receiving the signal of chemokines derived from platelets, and then other nonspecific factors with damage-associated molecular patterns (DAMPs) and pathogen-associated molecular patterns (PAMPs), released from dying cells and microbial invaders, respectively. The binding of these patterned factors to toll-like receptors (TLRs) stimulates and transforms macrophages into M1 macrophages, marking the start of inflammation for the removal of invaded microorganisms and cell debris. At this stage of inflammation, M1 macrophages function as "master regulators of inflammation and fibrosis." As inflammation proceeds normally, the dominant macrophage population shifts from an "inflammatory" phenotype: M1 like macrophages to a "tissue repair" phenotype: M2 like macrophages, characterized by secretion of various paracrine factors. These factors collectively promote angiogenesis and further proliferation of fibroblastic and other cells for the tissue repair. Shifting of M1 macrophages population to an M2 population marks the ending of inflammation and the beginning of tissue repair. A wound is then healed.

M1 macrophages possess bactericidal and anti-tumor activity and thus M1 macrophages are one of the main forces in innate immune responses to fight against the invading microorganisms and other cell abnormalities such as cancers. In some cancer situations, the tumor antigens are not exposed to the immune system or the tumor antigens are too weak. In these situations, M1 macrophages are usually the only fighting force against cancer through non-specific phagocytosis. Upon the activation, M1-like macrophages also secret extensive toxic mediators such as nitric oxide and reactive oxygen intermediates that directly kill the cancer cells and invading microorganisms. M1 macrophages, meanwhile, secret predominant TNF-α and IL-12 for a long period to activate adaptive immune responses. M1 macrophages, together with activated adaptive immune response, e.g., antigen-specific, Th1 and Tcytotoxic cells, form a strong immune network, to effectively fight against cancer cells and invading microorganisms.

TAMs and Cancer. In contrast, M2 macrophages are dominantly present in the healing process of inflammation when granulation tissue formation occurs. [3, Marelli et al., 4, Tariq et al., 5, Mills et al.]. One of the driving force for M1 to M2 shifting in normal inflammation process is the disappearance of the TRL ligands, such as patterned factors from invading microorganisms, LPS, and CpG. Without the stimulation of TRL ligands, M1 macrophages fade away, and M2 macrophages turn off damaging immune responses by producing anti-inflammatory cytokines such as IL-10, thus allowing initiation of healing. M2 macrophages then recruit fibroblasts and activate them to differentiate toward myofibroblasts that release proangiogenic factors to recruit endothelial progenitor cells and enable new vessel formation, finishing the tissue repair process.

In cancers, the tissue repair process never finishes and thus cancers are aptly called "wounds never healed". Circulating monocytes are first recruited into the tumor tissue through the effect of growth factors and chemokines such as CCL2, M-CSF, and VEGF. Hypoxia further promotes recruitment of monocytes into tumor sites. In the tumor microenvironment, tumor-derived factors initiate the polarization of monocytes to tumor-associated macrophages (TAMs). T AMs are M2-like-polarized cells. Tumor tissues have no invading microorganisms and thus have no TRL ligands (e.g. pathogen-associated molecular patterns) present in the tumor microenvironment. Due to the lack of TRL ligand stimulation, there is little stimulating force to drive macrophages transforming into M1 macrophages. On other hand, tumor cells secret factors that promote the polarization of M2 macrophages. As a result, M2 macrophages prevail in the tumor microenvironment over time.

Studies have clearly shown that TAMs became accomplices when they have been recruited and transformed in the tumor microenvironment. Macrophages have high degree of plasticity, and they are easily influenced by tumor cells and the tumor microenvironment to become the assistants or accomplices of the tumor cells. TAMs help the tumor cells to complete the tasks that the tumor cells need to accomplish but are unable to complete, for their survival and expansion. T AMs secrete growth factors and chemokines which lead to the expression of molecules that support the tumor cell growth and survival (through CXCL8, CXCL12 and growth factors); regulate matrix remodeling (through MMPS, TNF, and chimokines); promote angiogenesis (through VEGF, TNF, and chemokines); and enhance tumor invasion and metastasis (through MMPS, TNF, and chemokines). TAMs inhibit the activity of Th1 cells, enhance the recruitment of Th2 cells and Treg cells, and energize the naive T cells through the secretion of TGF-beta IL-18, IL-10 and CCL22.

It is seen that without the help of TAMs, tumor cells are not able to survive and metastasize into other tissues. According to Hanahan and Weinberg, cancer manifests as six essential physiologic hallmarks: (1) self-sufficiency in growth signals, (2) insensitivity to growth-inhibitory signals, (3) evasion of programmed cell death, (4) limitless replicative potential, (5) sustained angiogenesis, and (6) invasion and metastasis. [6, Hanahan and Weinberg] As a facilitator of these traits as well as immunosuppression and chemoresistance, the presence of TAMs can serve as the seventh hallmark of cancer. Given that TAMs play a most active role for tumor cells to posses these traits, the presence of TAMs can be seen as a hallmark for tumor cell survival and metastasis.

Anti-cancer strategies based on targeting TAMs. Realizing the importance of TAMs in the tumor progression, anti-cancer therapeutic strategies targeting TAMs have received attention. [3, Marelli et al., 4, Tariq et al.]. These strategies include: 1) Blocking the recruitment of monocytes to tumor sites. This strategy involves using different inhibitors and monoclonal antibodies to block the chemokines and growth factors (CCL2, CCLS, and VEGF). Multiple methods that inhibit CSF-1 receptors have also been developed. Radiation also inhibits the recruitment of monocytes; 2) Inhibiting M2 macrophage polarization. This strategy is accomplished by using monoclonal antibody, signal transduction molecule inhibitors; 3) Depleting of monocytes and TAMs by chemical drugs and toxin-conjugated monoclonal antibody; and 4) Promoting the M1 polarization. This goal is achieved by low dose irradiation, anti-IL-10 and anti-CD40 monoclonal antibodies. Recently, reprogramming of M2 into M1 has been performed through CpG DNA and anti-IL-10 in vitro stimulation. Reversing the polarization of TAM from M2 to M1 phenotype can inhibit tumor metastasis in BALB/c mice. Also, chlorogenic acid inhibits glioblastoma growth through repolarizing macrophage from M2 to M1 phenotype.

The binding of pathogen-associated molecular patterns (PAMPs) released from microbial invaders, to Toll like receptors is essential for M1 polarization. More than 100 years ago, Dr. William Coley used inactivated bacteria to inoculate patients with cancer and reached some degree of therapeutic purpose. This method has been abandoned in United States due to dangerous side effect. However, the concept that M1 polarization requires stimulation by PAMPs, recombinant and inactivated microorganisms, subunits, such as LPS and CpG, are subjected to substantial investigation and used as anti-cancer immunotherapy.

Methods and Therapies and Therapeutics of the Present Invention

An effective and simple method is therefore needed to accomplish goal of targeting macrophages to treat cancers and other M2 related diseases. The present invention is aimed to develop methods that can overcome the M2 dominated immune background to induce an M1 dominated immune response in vivo in M2 dominant patients. We have developed an in vivo approach using immune activated sera from a healthy individual with an M1 dominant immune background to "help" the induction of an M1 dominated immune response in M2 dominated patients. The methods of the present invention have follow features: 1) Effectiveness. The immune response capability in the patients with cancers is usually suppressed by abundantly existing M2 macrophages. It is otherwise difficult to induce an M1 dominated immune response on its own without intervention. We have developed methods with the "help" of immune activated sera from healthy individuals that greatly increase the chance of induction of an M1 dominated immune response in M2 dominated patients; and 2) Feasibility and simplicity. Both allogenic and xenogenic immune activated sera do not contain cells and thus there is no MHC mismatch issue. The cross species specificity of the cytokines make it possible for xenogenic immune activated sera to offer the M1 immune response help over other species. No in vitro transformation and amplification of macrophages are needed; 3) Safety. The immune activated allogenic or xenogenic sera offer "temporary help" to induce a long-lasting M1 dominated immune response in M2 dominated immune background individuals. The "adverse effect", if any, is temporary and fades away in few days; and 4) Broad-spectrum application. The present invention relates to the methods that can be used in various forms of cancer and other M2 macrophage related diseases, e.g., chronic viral infections, allergies, and asthma.

Methods of Induction of and M1-Dominated Immune Response in M2 Dominated Immune Background Human Patients or Animals In the patients or animals with cancers, particularly with late stage cancers, the immune responses are usually suppressed by the abundantly presented M2 macrophages locally (in tumor microenvironment), as well as systematically. The current immunotherapy regimens are usually inefficient to overcome M2 dominated immune backgrounds in patients with cancer and thus often fail to induce an M1 dominated immune response against cancer. The failure of induction of an M1 dominated immune response in these patients can be a cause of the failure of current existing tumor immunotherapies and for the recurrence of tumors.

Varies methods have being developed aiming to overcoming an M2-dominated immune background and to launch an M1-dominated immune response against tumors in these M2-dominated patients.

Methods targeted at TAMs have been developed as anti-tumor therapies. The methods include suppressing TAMs survival through chemical drugs and monoclonal antibodies, blocking tumor-promoting activity of TAMs, and inhibiting macrophage recruitment to the tumor sites. Enhancing M1 tumoricidal activity is another strategy. Recently repolarizing macrophages from M2 to M1 has been reported to inhibit the growth of glioblastoma. These methods, however, do not reach their affectivity in the clinic and need more studies for the development.

Methods have been developed to generate inactivated or recombinant microorganisms and these microorganisms (such as Coley toxin) have been used to immunized the patients with cancer, aimed to induce a strong M1 dominated immune response against cancer. These therapeutic goals have not been reached due to severe side effects which limit their use in the clinic.

Methods have been developed to adoptively transfuse the allogenic immunocompetent cells such as natural killer cells, to cancer patients, aimed to compensate suppressed autologous natural killer cells due to their M2 dominated immune background. An obstacle in the development of this method is the barrier of a major histocompatibility complex (MHC). The challenges of graft versus host disease (GVHD) needs to be solved before it can be routinely used in the clinic.

It is possible that the immune response background of an individual is the base for the induction of an efficient immune response against an immunogen. In patients with cancer, the immune background is dominated by abundantly existing M2 macrophages. The immunization in these patients usually leads to an M2-dominant immune response. The reason for the ineffective induction of an M1 dominated immune response in M2 dominated immune background individuals can be due to the lack of some M1 dominated immune response induction factor(s) in these patients. Hence, some outsource "help" is needed during immunization in these patients to overcome the M2-dominated immune response background and to induce an M1-dominated immune response.

It is also possible that the immune activated allogenic sera from a normal individual, whose has an immune response background and will produce an M1-dominated immune response upon the immunization with microorganism or adjuvants or infected with microorganisms, will help those patients with cancer to overcome their M2-dominated immune background and to induce an M1-dominated immune response.

It is also possible that the immune activated allogenic sera contain all necessary compounds, including but not limited to M1 prone cytokines, to effectively overcome the M2-dominated immune response background and to effectively induce an M1-dominated immune response, in these M2 dominated patients with cancer.

It is also possible that the "help activity" of the immune activated allogenic sera has a time window of effectiveness: their "help activity" starts from about 6 hours to about 14 days (about two weeks), also from about 8 hours to about 14 days (about two weeks), after immunization or infection. After about 14 days (about two weeks), the "help activity" will usually have vanished.

The transfusion of immune activated allogenic sera will not have MHC mismatch problems since the sera will not contain allogenic cells.

The immune activated allogenic sera can be administrated into a recipient as a therapeutic agent alone or in combination with the immunogen.

The immune activated allogenic sera can be administrated into a recipient as an adjuvant alone or in combination with T cell-specific specific antigens.

It is also possible that the immune activated sera from a xenogenic individual (a mammal or a bird), who's immune response is normal and will produce a M1-dominated immune response upon the immunization or infection with microorganisms, will help a xenogenic recipient (such as a human) who has an M2-dominated immune background, to produce an M1-dominated immune response.

It is also possible that the immune activated xenogenic sera contain all necessary components, including but not limited to M1 prone cytokines, to effectively overcome the M2 dominated immune response background and to effectively induce an M1-dominated immune response. It is also possible that the immune activated xenogenic cytokines can overcome the species specificity and effectively induce the M1 dominated immune response in patients with cancer.

The immune activated xenogenic sera have a time window of effectiveness: their activation ability starts from about 6 hours to about 14 days (about two weeks), also from about 8 hours to about 14 days (about two weeks), after immunization.

The transfusion of immune activated xenogenic sera will have less likelihood of suffering from the MHC mismatch problem since the xenogenic sera will not contain xenogenic cells.

The immune activated xenogenic sera can be administrated into a recipient as a therapeutic agent alone or in combination with the immunogen.

The immune activated xenogenic sera can be administrated into a recipient as an adjuvant alone or in combination with T cell-specific antigens.

It is also possible that in order to obtain the maximum effect of immune activated sera transfusions, the time course of collection and infusion of immune activated sera should mimic the natural course of induction of an immune response against an acute infection by virus or bacteria, such as the influenza virus.

It is also possible that the active "help" compounds in immune activated allogenic sera need to be defined. The identified active compounds are formulated into a formulation to be tested for their "help" activity of the induction of an M1 dominated immune response in a M2-dominated individual.

The formulations of active compounds can be used alone or in combination with the immunogen(s).

The formulations of active compounds can be used as adjuvants alone or in combination with T cell-specific antigens.

Methods of Treating Cancers and Other M2 Dominated Immune Related Disease.

The present invention is directly related to the methods for treating cancer and other M2 macrophage dominated diseases. The present invention offers merit methods from a totally new angle to treat the various forms of cancer. Unlike the other current existing treatment methods that are focused on the patients themselves to overcome the M2 dominated immune background, the present invention is seeking to utilize materials from healthy individuals for the purpose of breaking down the M2 dominated immune background in these patients with cancer.

Compared to other existing cancer treatment methods, the present invention has several advantages: 1) Effectiveness. The immune response capability in the patients with cancers is usually suppressed by abundantly existing M2 macrophages. It is otherwise difficult to induce an M1 dominated immune response on its own without intervention. We have developed methods with the "help" of immune activated sera from healthy individuals that greatly increase the chance of induction of an M1 dominated immune response in M2 dominated patients; and 2) Feasibility and simplicity. Both allogenic and xenogenic immune activated sera do not contain cells and thus there is no MHC mismatch issue. The cross species specificity of the cytokines make it possible for xenogenic immune activated sera to offer the M1 immune response help over other species; 3) Safety. The immune activated allogenic or xenogenic sera offer "temporary help" to induce a long-lasting M1 dominated immune response in M2 dominated immune background individuals. The "adverse effect", if any, is temporary and fades away in few days; and 4) Broad-spectrum application. The present invention relates to the methods that can be used in various forms of cancer and other M2 macrophage related diseases, e.g., chronic viral infections, allergies, and asthma.

Therapeutic Agents and Pharmaceutical Compositions

The therapeutic agents are the immune-activated allogenic sera from individuals who have a normal immune response background and have been immunized with immunogen(s) or naturally infected with microorganisms.

The immune activated allogenic sera are transfused into an M2 dominated individual (patient with cancer or other M2 related diseases) alone or with the immunogen(s).

Alternatively, he immune activated allogenic sera are transfused into an M2 dominated individual (patient with cancer or other M2 related diseases) alone or with T cell-specific antigen(s).

Alternatively, the immune activated allogenic sera can be incorporated into existing immunotherapies.

The therapeutic agents are the immune-activated xenogenic sera from individuals who have normal immune response background and have been immunized with immunogen(s). The sera are transfused into an M2 dominated individual (patient with cancer or other M2 related diseases) alone or with the immunogen (s).

The immune activated xenogenic sera are transfused into an individual (patient with cancer or other M2 related diseases) alone or with T cell-specific antigen(s). Alternatively, the immune activated xenogenic sera can be incorporated into existing immunotherapies.

The therapeutic agents are the formulations of active compounds identified from effective immune activated allogenic sera. The formulations can be used with or without immunogens or T cell antigens. The formulations can be incorporated into existing immunotherapy regimens.

The therapeutic agents are the formulations of active compounds identified from effective immune activated xenogenic sera. The formulations can be used with or without immunogens or T cell antigens. The formulations can be incorporated into existing immunotherapy regimens.

The T cell-specific antigens can induce T cell-specific immune responses.

The present invention is also related to an immunization schedule in which the therapeutic reagents are used in mimicking the natural course of induction an immune response against an acute infection by virus and bacteria.

The source of an active serum as described herein can be from mammals, particularly humans. A serum preparation as described herein can be produced from blood using conventional methods as known in the art such as centrifugation and filtration. A serum preparation can be further purified to remove undesired components e.g. infectious agents. A serum preparation can be optionally formulated with a suitable carrier as needed for purpose of administration. A typical route of administration is injection.

EXAMPLES

The following examples further describe and demonstrate embodiments within the scope of the present invention. The Examples are given solely for purpose of illustration and are not to be construed as limitations of the present invention, as many variations thereof are possible without departing from the spirit and scope of the invention.

In these examples, we used two strains of mice in an experimental model. We used LPS as immunogen. BALB/c mice are M2/Th2 prone mice upon the infection of bacteria and immunization with LPS. In contrast, C57BL/6 mice are M1/Th1 prone mice upon the infection of bacteria and immunization with LPS [7, Mills C D et al., 8, Watanabe H et al.]. We use C57BL/6 mice as the donors of immune activated allogenic sera and use BALB/c mice as the recipient of immune activated allogenic sera. To test whether the transfusion of LPS immunization activated C57BL/6 sera could help to induce an M1 dominated immune response in BALB/c mice that with or without immunization with LPS. Surprisingly, the transfusion of LPS immunization activated C57BL/6 sera into BALB/c mice leads to the induction of M1-dominated immune response in BALB/c mice comparing to the BALB/c mice immunized with LPS alone.

Materials and Methods:

Mice and antibodies: tC57/BL6 and BALB/c mice are hosted and fed in a hospital animal facility according to hospital experimental animal committee regulations. The antibody information is in Table 1. F4/80 and TNF-α double positive cells are defined as M1 macrophages and F4/80 and CD206 double positive cells are defined as M2 macrophages.

TABLE 1

The antibodies used to define M1 and M2 macrophages.

| | Markers | Antibody information | |
|---|---|---|---|
| M1 macrophage | F4/80&TNF-a | PE anti-mouse F4/80 APC anti-mouse TNF-a | eBioscience Cat#12-4801 eBioscience Cat# 17-7321-81 |
| M2 macrophage | F4/80&CD206 | PE anti-mouse F4/80 APC anti-mouse CD206 | eBioscience Cat#12-4801 Biolegend Cat #141708 |

Immunizations of mice and sera transfusion: The mice were immunized with LPS intravenously (i.v.) through the tail. It was necessary to first immunize both the BALB/c and C57BL/6 mice with three different (0.5 mg/kg, 1.5 mg/kg, and 4.5 mg/kg (LPS/body weight)) doses of LPS to define the half lethal dose of LPS. We found that LPS at 1.5 mg/kg is the dose mice can tolerate. We then used a 1.5 mg/kg dose in all subsequent experiments. At different time points, the C57/BL6 mice were sacrificed and sera was obtained; approximately 0.5 ml of serum was obtained from each C57BL/6 mice. The sera were then pooled and then aliquoted and subsequently transfused i.v. into the LPS-immunized BALB/c mice. The final dose was serum from one C57BL/6 mouse to one BALB/c mouse. Three transfusions were performed at the time points 8, 20, and 44 hours after LPS immunization. At 72 hours after immunization, the C57BL/6 and BALB/c mice were sacrificed, and their spleens were obtained for producing splenic cells suspensions for determination of M1 and M2 cell counts using the markers in Table 1.

Staining of Splenic Cells with M1 and M2 Markers.

1. Fixation and Permeabilize Cells.

Splenic suspension cells were produced. For fixing and permeabilizing cells, $10^6$ splenic cells were thoroughly resuspended in 250 μL of BD Cytofix/Cytoperm solution (cat. #) in 5 ml FACS tubes and incubated for 20 min on ice Note: Cell aggregation can be avoided by vortexing prior to the addition of the BD Cytofix/Cytoperm™ solution. The cells were washed twice in 1 ml 1×BD Perm/Wash™ buffers (10×BD Perm/Wash™ buffer (cat)), which can be used as the wash buffer and as the antibody diluent.

2. Stain for Intracellular Cytokines

The fixed/permeabilized cells were thoroughly resuspended in 100 μL of a saponin-containing buffer (e.g., BD Perm/Wash™ buffer), which also contained a predetermined optimal concentration of fluorescence-conjugated anti-F4/80 antibody and fluorescence-conjugated cytokine antibodies in accordance with the antibody data sheet for the suggested dilution of the antibody. The cells were incubated at 4° C. for 30 minutes in the dark. For the antibody combinations, see Table 1. The cells were washed twice with 1 ml of a 1× saponin-containing buffer (e.g, BD Perm/Wash™ buffer) and resuspend in a 0.3 ml FACS buffer prior to flow cytometric analysis.

Flow cytometric analysis and data analysis. The F4/80/TNF-α (M1 macrophages) and F4/80/CD206 (M2 macrophages) double positive splenic cell counts were determined with two color flow cytometric analyses using standard techniques. The relative M1 versus M2 ratio was calculated and used to determine whether an M1-dominated immune response or an M2-dominated immune response occurred.

Example 1: C57BL/6 Mice Produce M1-Dominated Immune Response and BALB/c Mice Produce M2 Dominated Immune Response, Upon the Immunization of LPS, Respectively This experiment is designed to test whether C57BL/6 mice and BALB/c mice can produce M1 dominated immune response and M2 dominated immune response, respectively, upon the immunization of LPS.

For doing experiments, 1.5 mg/kg of LPS is dissolved in 200 ul of PBS and i.v. injection into tail vain of mice are performed. The mice are kept for 3 days and splenic suspension cells are obtained and used for staining of markers to define M1 macrophages and M2 macrophages. F4/80 and TNF-α double staining are used for identifying M1 macrophages and F4/80 and CD206 double staining are used to identify M2 microphages. FACS analysis is performed to determine the percentage of M1 and M2 cells in different mice. The results in Table 2 show that C57BL/6 mice produced M1 dominated immune responses and BALB/c mice produce M2 dominated immune response, respectively.

TABLE 2

M1/M2 ratios in C57/BL6 and BALB/c miceupon the immunization of LPS.

| Mice and Treatment | M1 (F4+/80/ TNF-a+ splenic cells) | M2(F4/80+/ CD206+ splenic cells) | Ratio of M1/M2 |
| --- | --- | --- | --- |
| BALB/c (PBS) 2 mice | 2.2 | 6.8 | 0.32 |
| BALB/c (LPS) 3 mice | 3.6 | 22.0 | 0.16 |
| C57BL/6 (PBS) 2 mice | 2.0 | 18.0 | 0.11 |
| C57BL/6 (LPS) 3 mice | 17.2 | 19.3 | 0.89 |

Example 2: Transfusion of LPS-Immunized Sera from C57/BL6 Mice into LPS-Immunized BALB/c Mice Induced an M1-Dominated Immune Response in BALB/c Mice Next we analyzed whether transfusion of LPS-immunized sera from C57/BL6 into LPS-immunized BALB/c (LPS-BALB/c) mice can convert an M2-oriented immune response to an M1-dominated immune response in BALB/c mice with and without immunization with LPS. BALB/c mice and C57BL/6 mice were immunized with 1.5 mg/kg LPS via the tail in venous. At the time points of 8, 20, and 44 hours, respectively, five (5) LPS-immunized C57BL/6 mice were sacrificed and their sera were pooled and then divided into 5 eliquates and injected into 5 BALB/c mice via the tail vein. For 3 time points, total 15 C57BL/6 mice were used. At the 72 hour time point, the BALB/c mice were sacrificed and their splenic cells were obtained for staining to determine M1 and M2 macrophages counts. The M1/M2 ratios for the different groups are shown in Table 3. From Table 3, one can see that the BALB/c mice immunized with LPS and transfused with sera from LPS-immunized C57BL/6 mice (group 4) generated an M1-dominated immune response that was significantly higher that of the LPS-BALB/c mice (group 3) (p<0.05). Transfusion of such immunized sera into BALB/c mice that have not been immunized with LPS (group 2) does not significantly induce an M1-dominated immune response (p>0.05).

TABLE 3

M1/M2 ratios in BALB/c mice transfused with LPS-immunized sera from C57/BL6 mice.

| Group | Treatment of BALB/c Mice | M1(F4/80/ TNF-a) | M2(F4/80/ CD206) | M1/M2 ratio |
| --- | --- | --- | --- | --- |
| 1 | Control (4 mice) | 1.96 | 6.29 | 0.31 |
| 2 | Sera[1] | 3.26 | 9.19 | 0.35 |
| 3 | LPS (5 mice) | 16.9 | 29.9 | 0.56 |
| 4 | LPS + Sera[2] (5 mice) | 21.9 | 24.6 | 0.89[2] |

[1]Sera = Sera from LPS immunized C57BL/6 mice
[2]Compared to the mice that were only LPS immunized, the LPS + sera (from LPS immunized C57BL/6 mice) mice significantly denomstrated an M1-dominated immune response with statistical significance (p < 0.05).

Example 3: Transfusion of Sera from Non-Immunized C57/BL6 Mice and Sera from C57BL/6 Mice that had Received LPS Immunization 14 Days Prior into LPS-BALB/c Mice does not Induce an M1-Dominated Immune Response To determine whether or not sera from non-immunized C57BL/6 mice induces an M1-dominated immune response in BALB/c mice, BALB/c mice are immunized with 1.5 mg/kg LPS with and without receiving sera from non-immunized C57BL/6 mice (at the time points of 8, 20, and 44 hours, respectively). The results in Table 4 indicate that non-immunized sera does not significantly (p>0.05) induce an M1-dominated immune response in LPS-BALB/c mice (group 2 versus group 4).

Next, we determined whether or not sera from C57BL/6 mice that had received LPS immunization 14 days prior induces an M1-dominated immune response in BALB/c mice. BALB/c mice are immunized with 1.5 mg/kg LPS, with and without receiving sera from C57BL/6 mice that had received LPS immunization 14 days prior (at the time points of 8, 20, and 44 hours, respectively). The results in Table 4 indicate that sera from C57BL/6 that have received LPS immunization 14 days prior does not significantly (p>0.05) induce an M1-dominated immune response in LPS-BALB/c mice (group 2 versus group 5).

Only the sera from C57BL/6 mice that had received LPS immunization at the time points of 8, 20, and 44 hours before transfusion significantly (p<0.05) induced an M1-dominated immune response in LPS-BALB/c mice (Table 3 and group 2 versus group 3 of Table 4).

TABLE 4

M1/M2 ratios in LPS-BALB/c mice transfused with sera from LPS immunized, non-immunized, and LPS immunized 14 days prior C57BL/6 mice.

| Group (5 mice/group) | Treatment of BALB/c mice | M1 (F4+/80/ TNF-a) | M2 (F4/80+/ CD20) | M1/M2 ratio |
| --- | --- | --- | --- | --- |
| 1 | PBS | 4.1 | 7.1 | 0.58 |
| 2 | LPS | 7.1 | 12.6 | 0.56 |
| 3 | LPS + Sera A | 11.3 | 12.2 | 0.93 |
| 4 | LPS + Sera N | 8.1 | 13.9 | 0.58 |
| 5 | LPS + Sera O | 7.8 | 14.2 | 0.55 |

Sera A = Sera from C57BL/6 mice that had received LPS immunization at time points of 8, 20, and 44 hour, respectively.
Sera N = Sera from non-immunized C57BL/6 mice.
Sera O = Sera from C57BL/6 mice that had received LPS immunization 14 days prior.

Example 4: Preparation of and Formulation of Sera for Inducing an M1 Dominated Immune Response This example describes the preparation of a therapeutic serum of the present invention. Generally, the serum is obtained from a healthy donor that has been inoculated with an immunogen. The preparation of the immune active allogenic and xenogenic serum involves the following steps.

(a) Inoculating a healthy donor with a defined immunogen in a defined amount followed by a defined waiting period for the development of a response in the donor to the immunogen. The said healthy donor has a normal immune response after being inoculated by the said immunogen. In the examples of this invention, we have defined that the LIDS at 1.5 mg/kg dose induce an M1 dominated immune response in C57BL/6 mice (used as the healthy donor with a normal immune response). The waiting time is from 8 hours, 20 hours, and 44 hours after inoculation by the immunogen. We have shown that after a waiting period of longer than 14 days, the immune activity of the sera will have been lost and the LPS-BALB/c mice will have faded to induce the M1 dominated immune response (Table 4).

(b) Producing an immune active allogenic or xenogenic serum sample from whole blood, which is obtained from a healthy donor subject inoculated with an immunogen. Whole blood from C57BL/6 mice is collected in a covered test tube. After collection of the whole blood, the blood is left at room temperature for 15 minutes undisturbed for a clot to form. The blood is then centrifuged at 1,000-2,000×g for 10 minutes in a refrigerated centrifuge to remove the clot and all blood cells. The liquid component (serum) is immediately transferred into a clean polypropylene tube. The samples were maintained at 2-8° C. during handling. For our purposes, all cells (RBC, WBC and platelet) in the blood are removed together with the clot in the whole blood. This step is important to avoid potential graft versus host reaction (GVHR) after transfusion into a recipient.

In the experiments, we usually obtain about 0.15 ml of serum from one C57BL/6 mouse. The sera are diluted to 0.2 ml with PBS before transfusion. For convenience, we pooled 5 whole blood samples together and then centrifuged the sample to obtain sera, which are then divided into 5 aliquots and transfused into 5 BALB/c mice, respectively. In order to maintain maximum efficacy of the immune active sera, the transfusion into BALB/c mice is performed right away.

(c) Formulating the serum sample as an active ingredient in an effective amount to form a therapeutic serum preparation for use in transfusion into the M2 dominated individual to induce the desired M1 dominated immune response. The formulation steps include: 1) defining the immune activity of the sera with and without the use of the immunogen. 2) defining a sera transfusion schedule for achieving the maximum efficacy of the sera in combination with the immunogen; and 3) defining the dose of immune active serum to be transfused. In the experiments, the immune active sera are transfused in doses of 0.2 ml (0.15 ml sera+0.05 ml PBS) per mouse at 8, 20, and 44 hour time points after inoculation of the donor mice. The experiments have also shown that the recipient mice need to be immunized with the immunogen at the same time points when the donor mice are inoculated. The sera are of limited immune activity if the recipient mice (BALB/c mice) are not immunized with immunogen (Table 3).

In further embodiments, in human clinic use, the sera may need to be further concentrated or the fraction of albumin in the sera needs to be totally or partially removed to increase the immune activity of the sera or reduce potential side effects. A pharmaceutical composition of the therapeutic serum preparation can include additional components in various combinations. The active factors are selected from the group consisting of cytokines, chemokines, growth factors, macrophage activating factors, and enzymes.

The sera described herein are useful as a medicament for inducing an M1 dominated immune response, treating an M2 macrophage mediated disease state, and/or inducing a TH1 and cytotoxic immune response in a subject in need thereof, such as an M2 dominated patient or an M2/Th2 dominated patient.

Examples Discussion

The object of these experiments was to determine whether transfusion of allogenic immune activated sera induces an M1-dominated immune response in M2-dominated individuals. We used C57BL/6 and BALBC/c mice as allogenic strains to perform these experiments. Research [7 Mills C D et al., 8. Watanabe H et al.] has shown that C57BL/6 mice produce M1/Th1-dominated immune responses upon immunization with LPS or killed microorganisms, or infection of living microorganisms, while BALB/c mice produce M2/Th2-dominated immune responses upon immunization or infection with the same agents. We have demonstrated that immune activated sera from LPS immunized C57BL/6 mice can break down the M2 dominated immune background and induce an M1 dominated immune response in BALB/c mice. Our results show that the immune activated sera from LPS immunized C57BL/6 mice does induce an M1 dominated immune response in BALB/c mice with statistical significance.

M2 macrophages, also called tumor associated macrophages (TAMs) prevail in patients with tumors, particularly with late stage tumors. TAMs are necessary for tumor growth and tumor matastasis. TAMs also suppress the tumor-specific immune response in the body. Thus TAMs are a promising target for tumor immunotherapy. Other tumor iummunotherapy methods directly immunize tumor patients with M2 immune background and thus those methods usually induce an M2 dominated immune response, or at least failed to induce an M1 dominated immune response, contributing towards the failure of those immunotherapies. We hypothesize that sera from healthy individuals (help) is needed to breakdown the M2 dominated immune background and to induce an M1 dominated immune response in tumor patients with M2 dominated immune backgrounds. Data from these experiments confirm the underlying technology.

REFERENCES

1. Origin and functions of tissue macrophages. Epelman S, Lavine K L, Randolph G J. Immunity. 41(1):21-35 (2014).
2. The Promise of Targeting Macrophages in Cancer Therapy. Brown J M, Recht L, Strober S, Clin Cancer Res. 23(13):3241-3250 (2017).
3. Inflammation as target in cancer therapy. Marelli G, Sica A, Vannucci L, Allavena P. Curr Opin Pharmacol. 35:57-65 (2017).
4. Macrophage Polarization: Anti-Cancer Strategies to Target Tumor-Associated Macrophage in Breast Cancer. Muhammad Tariq, Jieqiong Zhang, Guikai Liang, Ling Ding, Qiaojun He, and Bo Yang. J Cell Biochem. 9999: 1-18 (2017).

5. A Breakthrough: Macrophage-Directed Cancer Immunotherapy. Mills C D, Lenz L L, Harris R A. Cancer Res. 76(3):513-6 (2016).
6. Hallmarks of Cancer: the next generation. Hanahan D, Weinberg R A. Cell. 144(5):646-74 (2011).
7. M-1/M-2 macrophages and the Th1/Th2 paradigm. Mills C D, Kincaid K, Alt J M, Heilman M J, Hill A M. J Immunol. 164(12):6166-73 (2000).
8. Innate immune response in Th1- and Th2-dominant mouse strains. Watanabe H, Numata K, Ito T, Takagi K, Matsukawa A. Shock. 22(5):460-6 (2004).

INCORPORATION BY REFERENCE

The entire disclosure of each of the patent documents, including certificates of correction, patent application documents, scientific articles, governmental reports, websites, and other references referred to herein is incorporated by reference herein in its entirety for all purposes. In case of a conflict in terminology, the present specification controls.

EQUIVALENTS

The invention can be embodied in other specific forms without departing from the spirit or essential characteristics thereof. The foregoing embodiments are to be considered in all respects illustrative rather than limiting on the invention described herein. In the various embodiments of the methods and compositions of the present invention, where the term comprises is used with respect to the recited steps or compositions, it is also contemplated that the methods and compositions consist essentially of, or consist of, the recited steps or components. Furthermore, the order of steps or order for performing certain actions is immaterial as long as the invention remains operable. Moreover, two or more steps or actions can be conducted simultaneously.

In the specification, the singular forms also include the plural forms, unless the context clearly dictates otherwise. Unless defined otherwise, all technical and scientific terms used herein have the same meaning as commonly understood by one of ordinary skill in the art to which this invention belongs. In the case of conflict, the present specification will control.

Furthermore, it should be recognized that in certain instances a composition can be described as being composed of the components prior to mixing, because upon mixing certain components can further react or be transformed into other materials.

All percentages and ratios used herein, unless otherwise indicated, are by weight.

What is claimed is:

1. A pharmaceutical composition for inducing an M1/Th1 dominated immune response in an M2/Th2 dominated patient comprising:
    (a) an allogenic immune active serum obtained from an M1/Th1 dominated healthy donor, wherein the donor has been immunized with an immunogen prior to obtaining the serum, and
    (b) an immunogen.

2. The pharmaceutical composition according to claim 1 comprising:
    a) active factors that are stimulated by immunization of heathy individual with the immunogen and that are essential for the induction of the M1/Th1 dominated immune response in the M2/Th2 dominated patient, wherein said active factors are selected from cytokines, chemokines, growth factors, macrophage activating factors, enzymes, and combinations thereof, and
    b) an immunogen.

3. The pharmaceutical composition according to claim 1 wherein the serum is obtained from a healthy donor previously inoculated with an immunogen, wherein the time schedule for obtaining the immune active serum sample and of subsequently transfusing the immune active serum are each individually selected from about 8 hours to about 14 days after inoculation of the healthy donor with the immunogen.

4. A pharmaceutical composition for treating an M2/Th2 disease state in an M2/Th2 dominated patient by inducing an M1/Th1 dominated immune response in an M2/Th2 dominated patient, said composition comprising:
    (a) an allogenic immune active serum obtained from an M1/Th1 dominated healthy donor, wherein the donor has been immunized with an immunogen prior to obtaining the serum, and
    (b) an immunogen,
    Wherein the disease state is selected from the group consisting of cancer and chronic viral infections.

* * * * *